United States Patent [19]

Fischer et al.

[11] 4,215,139

[45] Jul. 29, 1980

[54] CARBAMIC ACID DERIVATIVES

[75] Inventors: Ulf Fischer, Frenkendorf; Fernand Schneider, Basel; Rene Zurflueh, Bülach, all of Switzerland

[73] Assignee: Hoffmann-La Roche Inc., Nutley, N.J.

[21] Appl. No.: 18,026

[22] Filed: Mar. 6, 1979

[30] Foreign Application Priority Data

Mar. 17, 1978 [CH] Switzerland ..................... 2929/78

[51] Int. Cl.² .............. C07C 149/437; C07C 125/06; A01N 9/30; A01N 9/24
[52] U.S. Cl. ........................................ 424/300; 560/9; 560/12; 560/27; 560/17; 260/455 A; 260/465 E; 260/570.7
[58] Field of Search ............... 424/300; 560/9, 17, 560/27, 12; 260/455 A

[56] References Cited

U.S. PATENT DOCUMENTS

| | | | |
|---|---|---|---|
| 3,228,831 | 1/1966 | Nicholson | 560/9 |
| 3,600,437 | 8/1971 | Marshall | 560/9 |
| 3,649,679 | 3/1972 | Marshall | 560/9 |
| 3,769,319 | 10/1975 | Boltze | 424/300 |
| 3,801,624 | 4/1974 | Biel | 560/27 |
| 3,824,274 | 7/1974 | Franke | 560/9 |
| 3,900,507 | 8/1975 | Karrer | 560/17 |
| 4,017,536 | 4/1977 | Karrer | 560/17 |

*Primary Examiner*—Norman Morgenstern
*Assistant Examiner*—Michael Shippen
*Attorney, Agent, or Firm*—Jon S. Saxe; Bernard S. Leon; William M. Farley

[57] ABSTRACT

Carbamic acid derivatives, processes for their preparation, as well as pesticidal compositions containing the carbamic acid derivatives, and methods for their use, are disclosed.

33 Claims, No Drawings

CARBAMIC ACID DERIVATIVES

BACKGROUND OF THE INVENTION

U.S. Pat. No. 3,939,274 discloses insecticidal compositions containing, as the active ingredient, a compound of the formula

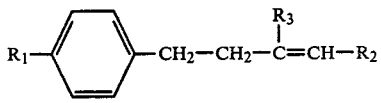

wherein, inter alia, $R_1$ is phenyl, phenoxy or phenylthio which may optionally be substituted, $R_2$ is carbamoyl, alkoxycarbonyl, alkylcarbamoyl or dialkyl-carbamoyl and $R_3$ is hydrogen or lower alkyl. German DOS No. 2,322,853 discloses compounds of the formula

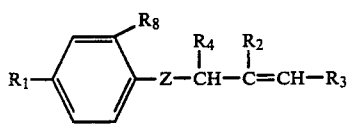

wherein, inter alia, $R_1$ is

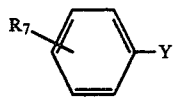

with Y either oxygen or methylene and $R_7$ is hydrogen, halogen, alkoxy or alkyl, Z is oxygen, $R_2$ is hydrogen or alkyl, $R_3$ is carboxyl, alkoxycarbonyl or substituted carbamoyl, $R_4$ is hydrogen, methyl or ethyl and $R_8$ is halogen, methyl or ethyl. Further, phenyl carbamates are known insecticides as described, for example, in German DOS No. 1,910,259, British Pat. No. 1,220,056, German DOS No. 2,341,949, German DOS No. 1,922,929, German DOS No. 2,311,384 and Pesticide Science 1972, 3, pp. 735-744. In addition, 2,3-(isopropylidenedioxy)phenyl-methyl [(trichloromethyl)thio]-carbamate and its use as an insecticide is disclosed in U.S. Pat. No. 4,005,216 while its use in a synergized insecticidal composition is disclosed in pending U.S. patent applications Ser. Nos. 4,517 and 4,521.

SUMMARY OF THE INVENTION

This invention relates to carbamic acid derivatives of the formula

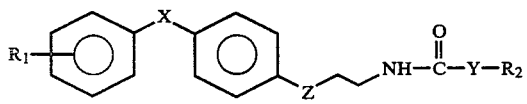

wherein $R_1$ is hydrogen, fluorine, chlorine, alkyl of from one to six carbons, trifluoromethyl, hydroxy or methoxy, X is oxygen, carbonyl, methylene, sulphur or sulphonyl, Z is oxygen, methylene, or sulphur, Y is oxygen or sulphur and $R_2$ is alkyl of from one to six carbons; and to processes for their preparation. This invention is also directed to pesticidal compositions containing, as the active ingredient, one or more compounds of formula I and methods for use of these pesticidal compositions.

DETAILED DESCRIPTION OF THE INVENTION

This invention is directed to carbamic acid derivatives of formula I above. This invention is also directed to processes for the preparation of the compounds of formula I.

Pesticidal compositions containing one or more compounds of formula I as well as methods for their use in the control of pests are also encompassed within the scope of this invention. The pesticidal activity of the compounds of formula I is achieved by interference with the hormonal system of the pest organism in contrast to the killing, crippling or repelling action of other pesticides.

The carbamic acid derivatives of formula I are prepared by one of the procedures described below:

A. The reaction of a phenol of the formula

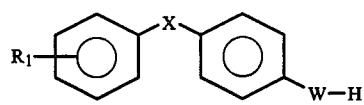

wherein $R_1$ and X have the same significance as reported earlier and W is oxygen or sulphur, with a halide of the formula

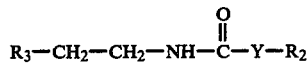

wherein

Y and $R_2$ have the same significance as reported earlier and $R_3$ is chlorine, bromine or iodine, The reaction of the phenol with the halide is carried out in an inert organic solvent, preferably dimethylformamide, dioxan, hexamethylphosphoric acid triamide, tetrahydrofuran, dimethoxyethane or a mixture of two or more of these solvents. The reaction is conveniently carried out in the presence of an alkali metal, an alkali metal hydride, an alkali metal amide, an alkali metal hydroxide or an alkali metal carbonate, and, preferably, potassium carbonate. Sodium and potassium are the preferred alkali metals.

The reaction temperature is not critical and can range from $-20°$ C. to the boiling point of the reaction mixture. The preferred reaction temperature is from room temperature to 100° C., with a temperature between 80° C. and 100° C. especially preferred. Where $R_3$ in formula III represents a bromine or iodine atom, the reaction temperature is somewhat lower, preferably room temperature.

The corresponding phenolate is formed from the phenol of formula II.

B. The reaction of an amine of the formula

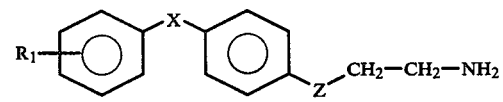

wherein $R_1$, X and Z have the same significances as reported earlier, with a compound of the formula

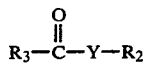

(V)

wherein
R$_2$ and R$_3$ have the same significance as reported earlier.

The reaction of the amine with a compound of formula V is carried out in an inert organic solvent (e.g. acetone) and, preferably, in the presence of a base such as an alkali metal carbonate, preferably potassium carbonate.

The reflux temperature of the reaction mixture is the preferred reaction temperature.

The reaction is usually complete after about one day. Any undissolved salts remaining are filtered from the reaction mixture. The filtrate is evaporated in vacuo and the residue is recrystallized.

C. Treatment of a thioether of the formula

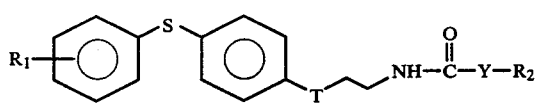

(VI)

where R$_1$, Y and R$_2$ have the same significance as reported earlier and T is oxygen or methylene, with a peracid.

The compound of formula VI is oxidized by the peracid to the corresponding sulfonyl compound. Especially suitable as the oxidizing agent are organic peracids, particularly m-chloroperbenzoic acid.

The oxidation is advantageously carried out in an inert organic solvent, especially in methylene chloride, at a temperature between 0° C. and room temperature.

To insure the complete oxidation of the sulfide sulfur atom to the sulfonyl group, at least 2 mols of the peracid are used for each mol of the thioether of formula VI.

Alkyl groups of from one to six carbons include methyl, ethyl, propyl, isopropyl, butyl, isobutyl, sec.butyl, tert.butyl, pentyl, isopentyl, hexyl, isohexyl and the like.

The preferred compounds of formula I are those wherein R$_1$ is hydrogen, Z is oxygen, X is oxygen, methylene or carbonyl, Y is oxygen and R$_2$ is ethyl or isopropyl.

The especially preferred compounds of formula I are:
2-[p-(p-chlorobenzoyl)phenoxy]ethylcarbamic acid ethyl ester,
2-(p-benzoylphenoxy)ethylcarbamic acid ethyl ester,
2-[p-(p-chlorobenzyl)phenoxy]ethylcarbamic acid ethyl ester,
2-[p-(o-chlorobenzoyl)phenoxy]ethylcarbamic acid ethyl ester,
2-[p-[(p-chlorophenyl)thio]phenoxy]ethylcarbamic acid ethyl ester,
2-[p-[(p-chlorophenyl)sulphonyl]phenoxy]ethylcarbamic acid ethyl ester,
2-[p-(p-toluoyl)phenoxy]ethylcarbamic acid ethyl ester,
2-[p-(p-tolyloxy)phenoxy]ethylcarbamic acid ethyl ester,
2-[p-(m-toluoyl)phenoxy]ethylcarbamic acid ethyl ester,
2-[p-(o-toluoyl)phenoxy]ethylcarbamic acid ethyl ester,
2-[p-(p-hydroxybenzoyl)phenoxy]ethylcarbamic acid ethyl ester,
2-(p-benzylphenoxy)ethylcarbamic acid ethyl ester,
2-(p-benzoylphenoxy)ethylthiocarbamic acid S-ethyl ester,
2-[p-(phenylsulphonyl)phenoxy]ethylcarbamic acid ethyl ester,
2-[p-(phenylthio)phenoxy]ethylcarbamic acid S-ethyl ester,
2-[p-(phenylthio)phenoxy]ethylthiocarbamic acid S-ethyl ester,
2-[p-(p-chlorophenoxy)phenoxy]ethylcarbamic acid ethyl ester,
2-[p-(p-chlorophenoxy)phenoxy]ethylcarbamic acid isopropyl ester,
2-(p-phenoxyphenoxy)ethylcarbamic acid ethyl ester,
2-[p-(m-tolyloxy)phenoxy]ethylcarbamic acid ethyl ester, and
2-[p-(p-tert.butylphenoxy)phenoxy]ethylcarbamic acid ethyl ester.

This invention is also directed to pesticidal compositions which comprise inert carrier material and, as the active ingredient, one or more of the compounds of formula I as well as methods for their use in the control of pests.

Most known pesticides function as contact and feed poisons by destroying, impeding or repelling pests. The compounds of formula I, however, function as pesticides by interfering with the hormonal system of pests. With insects, for example, the metamorphosis to the imago, the laying of viable eggs and the development of normal laid eggs is disturbed. Thus, the sequence of generations is interrupted and the pests are indirectly killed.

The compounds of formula I are practically nonpoisonous to vertebrates with the toxicity range above 1000 mg/kg body weight. The compounds of formula I are readily degraded and, therefore, the danger of accumulation is minimized. Further, these compounds can accordingly be used safely to control pests on animals, plants, and provisions as well as in water.

The pesticidal compositions of this invention are suitable for the control of invertebrates, particularly of arthropods and nematodes and especially of insects of the orders Diptera, Lepidoptera, Homoptera, Hymenoptera, Coleoptera, Orthoptera, Heteroptera, Psocoptera, Thysanoptera, Neuroptera and Blattida, of arachnida of the order Acarina and of nematodes of the order Tylenchida. Their activity against mosquitoes and Homoptera is a preferred aspect of the present invention.

Examples of such insects are:

| | |
|---|---|
| *Aedes aegypti* | Yellow fever mosquito |
| *Culex pipiens* | Common house mosquito |
| *Aedes taeniorrhynchus* | |
| *Anopheles stephensi* | |
| *Calliphora sp.* | |
| *Musca domestica* | Common house fly |
| *Adoxophyes reticulana* | Summer fruit tortrix moth |
| *Ephestia Kuhniella* | Mediterranean flyor moth |
| *Galleria mellonella* | Wax moth, greater |
| *Heliothis virescens* | |
| *Laspeyresia pomonella* | Codling moth, fruit maggot |
| *Choristoneura fumiferana* | North American spruce budworm |
| *Argyrotenia velutinana* | |
| *Synanthedon pictipes* | |
| *Lobesia botrana* | Grape tortrix moth |
| *Ostrinia nubilalis* | European core borer |

| | |
|---|---|
| *Plodia interpunctella* | Indian-meal moth |
| *Plutella xylostella* | Diamond-black moth |
| *Spodoptera littoralis* | Egyptian cotton leafworm |
| *Tineola biselliella* | Common clothes moth |
| *Bucculatrix thurberiella* | Cotton leaf perforator |
| *Aphis fabae* | Bean aphid, black |
| *Aphis pomi* | Green apple aphid |
| *Aonidiella aurantii* | Californian red scale |
| *Quadraspidiotus perniciosus* | San-Jose scale |
| *Unaspis citri* | |
| *Saissetia oleae* | Black olive scale |
| *Aspidiotus hederae* | Oleander scale |
| *Coccus hesperidum* | Soft scale |
| *Myzus persicae* | Peach-potato aphid |
| *Planococcus citri* | Citrus mealybug |
| *Megoura viciae* | |
| *Trialeurodes vaporariorum* | Glasshouse whitefly |
| *Laodelphax striatellus* | Grain cicad |
| Rhizoecus sp. | Root infesting mealybugs |
| *Dermestes maculatus* | Leather beetle |
| *Epilachna chrysomelina* | Cucumber beetle, spotted |
| *Leptinotarsa decemlineata* | Colorado potato beetle |
| *Oryzaephilus surinamensis* | Saw-toothed grain beetle |
| *Otiorrhynchus sulcatus* | Vine weevil, sulcate |
| *Rhizopertha dominica* | Lesser grain borer |
| *Sitophilus granarius* R + S | Grain weevil, common |
| *Sitophilus oryzae* R + S | Lesser rice weevil |
| *Tenebrio molitor* | Yellow mealworm, beetle, common |
| *Tribolium castaneum* R + S | Flour beetle, red-brown |
| *Trogoderma granarium* | Khapra beetle |
| *Blatella germanica* | German cockroach (cockroach beetle) |
| *Leucophaea surinamensis* | |
| *Nauphoeta cinerea* | Grey cockroach |
| Psylla spp. | Leaf sucker |
| *Blatta orientalis* | |
| *Periplaneta americana* | |
| *Dysderous cingulatus* | Cotton bug, cotton stainer |
| *Rhodinus prolixus* | Kissing bug |
| *Tetranychus urticae* | Two-spotted spider mite |
| *Tetranychus cinnabarinus* | Carmine spider mite |
| *Phytoseiulus macrophilis* | Robber mite |
| *Panonynchus ulmi* | |
| *Ditylenchus dipaci* | Stem eelworm |
| *Heterodera cruciferae* | Brassica cyst eelworm |
| Meloidogyne sp. | Root knot eelworm |

R = resistant strain
S = sensitive strain

The pesticidal compositions of this invention can be used as concentrates, granulates or, together with inert carrier material, in the form of sprays, aerosols or powders. For certain uses it is advantageous to use the compositions in the form of emulsions or solutions which contain emulsifying or wetting agents.

Examples of inert carrier materials suitable for use as solid carriers are chalk, talc, bentonite, kaolin, diatomaceous earth, siliceous earth, Fullers earth, lime, gypsum, powders and dusts from organic waste products, polymers (e.g. polyvinyl chloride, polyethylene, polyacrylate, polystyrene and mixed polymerisates) and the like.

The pesticidal compositions can also contain, as carrier material, additives such as antioxidants, UV-absorbers and other stabilizers, as well as odorant substances, baits etc.

The pesticidal compositions can also be in a form (e.g. microcapsules, coated granulates, solutions in polymeric substances, etc) whereby the active substance is released at a fixed rate in certain dosages.

These pesticidal compositions are usually prepared by mixing inert carrier material with one or more of the compounds of formula I.

In general, the pesticidal compositions of this invention can be prepared following the procedures described, for example, in Farm Chemicals, Volume 128, page 52 et seq.

The instant pesticidal compositions can also contain other additives such as emulsifiers or masking agents.

The pesticidal compositions can be prepared as concentrates suitable for storage and transport. Such concentrates can contain, for example, 25–90% of active substance (i.e. one or more of the compounds of formula I). Granulates usually contain 1–5% of active substance and are preferably used in the control of mosquitoes. These concentrates can be diluted, just prior to use, with the same or different carrier materials to provide concentrations which are suitable for practical use.

A ready-to-use pesticidal composition for spraying can contain, for example, an active substance concentration of 0.01–0.5%, preferably 0.1%. The active substance concentration can, however, also be lower or higher depending on such factors as the method of use, the pests to be controlled and the like.

A oncentration of active ingredient of from about $10^{-6}$ to about $10^{-4}$ g/cm$^2$ or less, i.e., spray liquor concentration of from about 0.1% to about 10% by weight, or less, is sufficient to achieve the desired pesticidal effect.

The pesticidal compositions provided by the present invention can be used against pests following the usual procedures such as, for example, by contact or by intake with the feed.

The compounds of formula I are also suitable as additives to the feed of silkworms and can be used in silkworm farming to improve the quality of the silk thread.

The following Examples illustrate the invention.

EXAMPLE 1

10 g of p-hydroxybenzophenone are dissolved in 100 ml of dimethylformamide. 8.3 g of 2-chloroethylcarbamic acid ethyl ester and 13.8 g of potassium carbonate are added to the solution and the mixture is warmed to 100° C. and maintained there for 3 hours with stirring. The mixture is poured onto an ice/water bath. The resulting crystals are filtered and washed with water. The crystalline substance is dried at 40° C. in a vacuum drying oven. Recrystallization once from ether yields 12.5 g (80%) of 2-(p-benzoylphenoxy)ethylcarbamic acid ethyl ester, m.p.—84°–86° C.

In an analogous manner:

2-[p-(p-hydroxybenzoyl)phenoxy]ethylcarbamic acid ethyl ester, m.p.—114°–115° C. (from ether), is prepared from p-(p-hydroxybenzoyl)phenol and 2-chloroethylcarbamic acid ethyl ester;

2-(p-benzylphenoxy)ethylcarbamic acid ethyl ester, m.p.—61°–63° C. (from ether), is prepared from p-benzylphenol and 2-chloroethylcarbamic acid ethyl ester and 2-[p-(p-phenylthio)-phenoxy]ethylcarbamic acid ethyl ester, m.p.—below 20° C., is prepared from p-(phenylthio)phenol and 2-chloroethylcarbamic acid ethyl ester.

EXAMPLE 2

5.5 g of 2-(p-benzoylphenoxy)ethylamine and 13 g of chloroformic acid ethyl ester are dissolved in 200 ml of acetone. 19.3 g of potassium carbonate are added to the solution and the mixture is heated under reflux with stirring for 30 hours. The mixture is then filtered and the crystals are washed with acetone. The filtrate is evaporated in vacuo. The residue is dissolved in ethyl acetate. The organic phase is washed with water, dried over sodium sulfate and evaporated in vacuo. The residue is dissolved in ether and crystallized by the addition of cyclohexane to yield 3.8 g (61%) of 2-(p-benzoylphenoxy)ethylcarbamic acid ethyl ester, m.p.—84°-86° C.

In an analogous manner:

2-[p-(p-chlorobenzoyl)phenoxy]ethylcarbamic acid ethyl ester, m.p.—136°-137° C. (from ethyl acetate/ether), is prepared from 2-[p-(p-chlorobenzoyl) phenoxy]ethylamine and chloroformic acid ethyl ester;

2-[p-(p-chlorobenzyl)phenoxy]ethylcarbamic acid ethyl ester, m.p.—81°-82° C. (from ether/cyclohexane), is prepared from 2-[p-(p-chlorobenzyl) phenoxy]ethylamine and chloroformic acid ethyl ester;

2-[p-(o-chlorobenzoyl)phenoxy]ethylcarbamic acid ethyl ester, m.p.—82°-83° C. (from ether/cyclohexane), is prepared from 2-[p-(o-chlorobenzyl) phenoxy]ethylamine and chloroformic acid ethyl ester;

2-[p-[(p-chlorophenyl)thio]phenoxy]ethylcarbamic acid ethyl ester, m.p.—71°-72° C. (from ether/low boiling petroleum ether), is prepared from 2-[p-[(p-chlorophenyl) thio]phenoxy]ethylamine and chloroformic acid ethyl ester;

2-[p-(p-toluoyl)phenoxy]ethylcarbamic acid ethyl ester, m.p.—85°-87° C. (from ether), is prepared from 2-[p-(p-toluoyl)phenoxy]ethylamine and chloroformic acid ethyl ester;

2-[p-(p-tolyloxy)phenoxy]ethylcarbamic acid ethyl ester, m.p.—78°-79° C. (from ether), is prepared from 2-[p-(p-tolyloxy)phenoxy]ethylamine and chloroformic acid ethyl ester;

2-[p-(m-toluoyl)phenoxy]ethylcarbamic acid ethyl ester, m.p.—84°-86° C. (from ether/low boiling petroleum ether), is prepared from 2-[p-(m-toluoyl)phenoxy]ethylamine and chloroformic acid ethyl ester and 2-[p-(o-toluoyl)phenoxy]ethylcarbamic acid ethyl ester, m.p.—72°-73° C. (from ether/low boiling petroleum ether), is prepared from 2-[p-(o-toluoyl)phenoxy]ethylamine and chloroformic acid ethyl ester.

EXAMPLE 3

3.5 g of 2-[p-[(p-chlorophenyl)thio]phenoxy]ethylcarbamic acid ethyl ester are dissolved in 43 ml of chloroform. 4.3 g of m-chloroperbenzoic acid are added portionwise with stirring to the solution over a 15 minute period. After the addition is complete, the mixture is stirred at room temperature for additional 2 hours, the crystals are filtered and the filtrate is washed with 2-N sodium hydroxide. The organic phase is dried over sodium sulfate and evaporated under vacuum. The residue is recrystallized from ether to yield 3.6 g (94%) of 2-[p-[(p-chlorophenyl)sulfonyl]phenoxy]ethylcarbamic acid ethyl ester, m.p.—120°-121° C.

EXAMPLE 4

4 g of 2-[(p-phenoxy)phenoxy]ethylamine and 11.2 g of chlorothioformic acid S-ethyl ester are dissolved in 150 ml of acetone. 14.5 g of potassium carbonate are added to the solution. This mixture is heated under reflux for 6 hours and then filtered. The residue is washed with acetone and the filtrate is evaporated in vacuo. The crystalline residue is suspended in cyclohexane and filtered to yield 2.5 g (53%) of 2-[(p-phenoxy)phenoxy]ethylthiocarbamic acid S-ethyl ester, m.p.—56°-58° C.

EXAMPLE 5

4.7 g of 2-[p-(phenylthio)phenoxy]ethylcarbamic acid ethyl ester are dissolved in 47 ml of chloroform. 6.4 g of m-chloroperbenzoic acid are added portionwise with stirring to the solution so that the temperature does not rise above 40° C. After the addition is complete, the mixture is stirred at room temperature for additional 2 hours. The crystals are filtered and washed with chloroform. The filtrate is washed three times with 2-N sodium hydroxide and once with water and dried over sodium sulfate. The organic phase is evaporated in vacuo. The residue is crystallized from acetone to yield 2.8 g (50%) of 2-[p-(phenylsulfonyl)phenoxy]ethylcarbamic acid ethyl ester, m.p.—100°-101° C.

EXAMPLE 6

6.4 g of 2-(p-benzoylphenoxy)ethylamine and 17.2 g of chlorothioformic acid S-ethyl ester are dissolved in 230 ml of acetone, 22.2 g of potassium carbonate are added to the solution. The mixture is heated under reflux for 6 hours. After cooling to room temperature, the mixture is filtered, the residue is washed with acetone and the filtrate is evaporated in vacuo. The residue is suspended in hot ether and filtered. The residue is then washed with ether and the filtrate is evaporated in vacuo. Recrystallization of the residue from ether yields 2-(p-benzoylphenoxy)ethylthiocarbamic acid S-ethyl ester, m.p.—90°-92° C. Recrystallization of the mother liquor yields a further 1 g of product.

EXAMPLE 7

7 g of 2-[p-(phenylthio)phenoxy]ethylamine and 18.6 g of chlorothioformic acid S-ethyl ester are dissolved in 250 ml of acetone. 24 g of potassium carbonate are added to the solution and the mixture is heated under reflux for 6 hours. The mixture is then filtered, the residue is washed with acetone and the filtrate is evaporated in vacuo. The 13 g of residue are filtered through a 10-fold amount of silica gel with ether/cyclohexane (7:3). The first fractions yielded 10.2 g which, after recrystallization from ether/low boiling petroleum ether yields 6.3 g (76%) of 2-[p-(phenylthio)phenoxy]ethylthiocarbamic acid S-ethyl ester, m.p.—77°-79° C.

EXAMPLE 8

10.88 g of a 50% sodium hydride suspension in mineral oil are diluted with 230 ml of absolute dimethylformamide and treated within 30 minutes with a solution of 50 g of p-(p-chlorophenoxy)phenol in 230 ml of absolute dimethylformamide while the temperature rises slightly. The mixture is then stirred at room temperature for 30 minutes. A solution of 18.8 g of chloroacetonitrile in 200 ml of absolute dimethylformamide is added dropwise while cooling the mixture in a waterbath. The mixture is stirred at 50° C. overnight, then cooled and diluted with 1 liter of water. This mixture is extracted five times with 200 ml of ethyl acetate each time. The organic phases are washed twice with 100 ml of 2-N sodium carbonate solution, once with 100 ml of saturated sodium chloride solution and then dried over magnesium sulfate and evaporated. The crude product (80 g of a dark oil) is purified by chromatography on silica gel using toluene for the elution to yield 45 g of [p-(p-chlorophenoxy)phenoxy]acetonitrile (76%) as a colorless oil.

Diborane (prepared from 69 g of sodium borohydride and 487 ml of boron trifluoride etherate) is added, while cooling with ice, into a solution of 45 g of [p-(p-chlorophenoxy)phenoxy]acetonitrile in 850 ml of absolute tetrahydrofuran. The mixture is stirred at room temperature overnight. The mixture is then cautiously acidified with 690 ml of 2-N hydrochloric acid and extensively concentrated in vacuo on a rotary evaporator. The residue is suspended in 300 ml of water, covered with 900 ml of toluene and made alkaline with 2-N sodium hydroxide. After the organic phase is separated, the aqueous phase is extracted twice with toluene. The combined toluene phases are washed neutral with saturated sodium chloride solution, dried over magnesium sulfate and evaporated in vacuo. The oily residue is taken up in ethanol, and acidified with hydrochloric acid in ether. The 2-[p-(p-chlorophenoxy)phenoxy]ethylamine hydrochloride which separates is recrystallized from alcohol/ether to yield 36.5 g (70%) of the colorless crystalline product, m.p.—217°-220° C.

18.4 g of potassium carbonate, 8.0 g of 2-[p-(p-chlorophenoxy)phenoxy]ethylamine hydrochloride and 16.0 g of chloroformic acid ethyl ester in 210 ml of acetone are heated to reflux with stirring for 7 hours. Undissolved salt is vacuum filtered and washed well with acetone. The filtrate is evaporated in vacuo. The crystalline residue remaining is dissolved in ethyl acetate, washed with water and saturated sodium chloride solution, dried over magnesium sulfate and concentrated. The residue is recrystallized from diisopropyl ether to yield 7.3 g (81.5%) of 2-[p-(p-chlorophenoxy)phenoxy]ethylcarbamic acid ethyl ester, m.p.—99°-100° C.

In an analogous manner, 2-[p-(p-chlorophenoxy)phenoxy]ethylcarbamic acid isopropyl ester, m.p.—88°-89° C. (from diisopropyl ether), is prepared from 2-[p-(p-chlorophenoxy)phenoxy]ethylamine hydrochloride and chloroformic acid isopropyl ester.

EXAMPLE 9

9.3 g of p-(p-phenoxy)phenol, 15.1 g of 2-(chloroethyl)carbamic acid ethyl ester and 27.6 g of potassium carbonate are stirred at 110° C. in 150 ml of dimethylformamide for 5 hours. The mixture is diluted with 300 ml of ice/water and extracted three times with 200 ml of ether each time. The organic phase is washed twice with 100 ml of 2-N sodium hydroxide each time and twice with 100 ml of saturated sodium chloride solution each time, dried over magnesium sulfate and evaporated in vacuo. The residue is recrystallized from petroleum ether to yield 11.6 g (77%) of 2-(p-phenoxyphenoxy) ethylcarbamic acid ethyl ester, m.p.—53°-54° C.

In an analogous manner:
2-[p-(m-tolyloxy)phenoxy]ethylcarbamic acid ester ($n_D^{20}$=1.5532) is prepared from p-(m-tolyloxy)phenol and (2-chloroethyl)carbamic acid ethyl ester and
2-[p-(p-tert.butylphenoxy)phenoxy]ethylcarbamic acid ethyl ester as a yellow oil ($n_D^{20}$=1.5436) is prepared from 4-[4-(1,1-dimethylethyl)phenoxy]phenol and (2-chloroethyl)carbamic acid ethyl ester.

EXAMPLE 10

In this Example, and in Examples 11-18 which follow, the compounds of formula I, as listed below, will be identified by the corresponding letters.

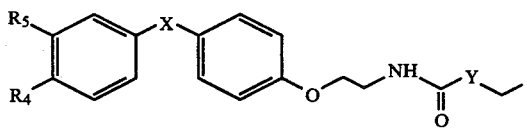

| Active Ingredient | R₅ | R₄ | X | Y |
|---|---|---|---|---|
| A | —H | —H | —O— | —O— |
| B | —H | —H | —C(=O)— | —O— |
| C | —CH₃ | —H | —O— | —O— |
| D | —H | —H | CH₂— | —O— |
| E | —H | —H | —O— | —S— |
| F | —H | —CH₃ | —O— | —O— |
| G | —H | —Cl | —CH₂— | —O— |
| H | —H | —Cl | —S— | —O— |
| I | —H | —Cl | —SO₂— | —O— |
| J | —H | —C(CH₃)₃ | —O— | —O— |
| K | —H | —H | —S— | —O— |
| L | —H | —H | —SO₂— | —O— |

The following compounds, identified in this Example and in Examples 11-18 by the corresponding letters, were also tested.

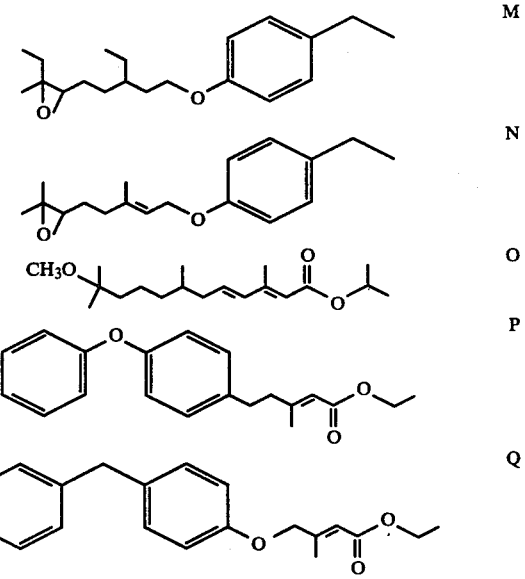

0.2 ml of an acetone solution of an active ingredient listed in Table I is mixed with 20 ml of tap water. To each solution, 10 larvae of Aedes aegypti (yellow fever mosquito) in the last larval stage are placed. The larvae are incubated at 25° C. and 60% relative humidity until the adults in the control solutions hatch. Both untreated (water) solutions and solutions treated with acetone only served as controls. The test period lasted seven days. The results, tabulated in Table 1, are expressed as the percentage reduction in the number normal adults in comparison with the controls (control mortality is 5%).

Table I

| Active Ingredient | Dosage $10^{-x}$ g. a.i./ml. water | % Reduction |
|---|---|---|
| A | 7 | 100 |
|  | 8 | 100 |
|  | 9 | 100 |
|  | 10 | 95 |

Table I-continued

| Active Ingredient | Dosage $10^{-x}$g. a.i./ml. water | % Reduction |
|---|---|---|
|  | 11 | 0 |
| E | 7 | 100 |
|  | 8 | 100 |
|  | 9 | 100 |
|  | 10 | 95 |
|  | 11 | 32 |
| M | 7 | 100 |
|  | 8 | 0 |
| N | 7 | 100 |
|  | 8 | 100 |
|  | 9 | 48 |
|  | 10 | 0 |
| O | 7 | 100 |
|  | 8 | 85 |
|  | 9 | 80 |
|  | 10 | 8 |
| P | 7 | 78 |
|  | 8 | 45 |
|  | 9 | 0 |
| Q | 7 | 95 |
|  | 8 | 44 |
|  | 9 | 0 | a.i. = active ingredient

EXAMPLE 11

Test method: 0.2 ml of an acetone solution of an active ingredient is mixed with 20 ml of tap water in a tablet tube. The thus-treated water is incubated for 7 days under UV light. Subsequently 10 larvae of *Aedes aegypti* (yellow fever mosquito) in the last larval stage are placed in each solution. The larvae are further incubated at 25° C. and 60% relative humidity until the adults in the control solution hatch. Untreated (water) solutions and solutions treated with acetone only served as controls. The duration of the test lasted for 7 days under UV light plus an additional 7 days. The results, reported in Table II, are expressed as the percentage reduction in the number of normal adults in comparison with the controls (untreated control mortality is 3%).

Table II

| Active Ingredient | Dosage $10^{-x}$g. a.i./ml. water | % Reduction |
|---|---|---|
| A | 7 | 100 |
|  | 8 | 100 |
|  | 9 | 100 |
|  | 10 | 0 |
| B | 7 | 100 |
|  | 8 | 40 |
|  | 9 | 18 |
| C | 7 | 100 |
|  | 8 | 100 |
|  | 9 | 0 |
| D | 7 | 100 |
|  | 8 | 100 |
| J | 7 | 100 |
|  | 8 | 50 |
| K | 7 | 100 |
|  | 8 | 39 |
| M | 7 | 73 |
|  | 8 | 9 |
| N | 7 | 100 |
|  | 8 | 0 |
| O | 7 | 15 |
|  | 8 | 0 |
| P | 7 | 9 |
|  | 8 | 0 |
| Q | 7 | 19 |
|  | 8 | 3 |

EXAMPLE 12

Test method: 1 ml of a solution of the active ingredient is mixed with 100 ml of tap water. 10 larvae of Culex pipiens (common house mosquito) in the last larval stage are placed in each solution. The larvae are incubated at 25° C. and 60% relative humidity until the adults in the control solutions hatch. Untreated (water) solutions and solutions treated with acetone served as controls. The duration of the test is 7 days. The results, tabulated in Table II, are expressed as the percentage reduction in the number of normal adults in comparison with the controls (control mortality is 5%)

Table III

| Active Ingredient | Dosage ($10^{-x}$g. a.i./ml water) | % Reduction |
|---|---|---|
| A | 7 | 100 |
|  | 8 | 100 |
|  | 9 | 100 |
|  | 10 | 46 |
|  | 11 | 0 |
| B | 7 | 100 |
|  | 8 | 100 |
|  | 9 | 100 |
|  | 10 | 14 |
| D | 7 | 100 |
|  | 8 | 100 |
|  | 9 | 85 |
|  | 10 | 43 |
|  | 11 | 0 |
| M | 7 | 100 |
|  | 8 | 0 |
| N | 7 | 100 |
|  | 8 | 100 |
|  | 9 | 30 |
|  | 10 | 0 |
| O | 7 | 100 |
|  | 8 | 100 |
|  | 9 | 63 |
|  | 10 | 15 |

EXAMPLE 13

Test method: 10 larvae of *Adoxophyes-reticulana* (Summer fruit tortrix moth) in the last larval stage are placed in Petri dishes, which had previously been treated with an acetone solution of the active ingredient in the quantities listed in Table IV. The larvae are fed with artifical nutrient medium and incubated at 25° C. and 60% relative humidity until the adults in the control dishes hatch. Untreated Petri dishes and Petri dishes treated with acetone served as controls. The duration of the test was 15-20 days. The results, tabulated in Table IV, are expressed as the percentage reduction in the number of normal adults in comparison with the controls (control mortality is 7%)

Table IV

| Active Ingredient | Dosage ($10^{-x}$g. a.i./cm$^2$ | % Reduction |
|---|---|---|
| A | 7 | 100 |
|  | 8 | 100 |
|  | 9 | 85 |
|  | 10 | 38 |
|  | 11 | 0 |
| C | 7 | 100 |
|  | 8 | 100 |
|  | 9 | 100 |
|  | 10 | 95 |
|  | 11 | 35 |
| D | 7 | 100 |
|  | 8 | 100 |
|  | 9 | 32 |
|  | 10 | 0 |

Table IV-continued

| Active Ingredient | Dosage ($10^{-x}$ g. a.i./cm$^2$) | % Reduction |
|---|---|---|
| G | 7 | 100 |
|   | 8 | 100 |
|   | 9 | 100 |
|   | 10 | 13 |
| H | 7 | 100 |
|   | 8 | 100 |
|   | 9 | 100 |
|   | 10 | 59 |
|   | 11 | 8 |
| I | 7 | 100 |
|   | 8 | 100 |
|   | 9 | 100 |
|   | 10 | 64 |
|   | 11 | 0 |
| L | 7 | 100 |
|   | 8 | 100 |
|   | 9 | 74 |
| K | 7 | 100 |
|   | 8 | 100 |
|   | 9 | 68 |
| M | 7 | 100 |
|   | 8 | 93 |
|   | 9 | 11 |
| N | 7 | 82 |
|   | 8 | 40 |
|   | 9 | 0 |
| O | 7 | 80 |
|   | 8 | 0 |
| P | 7 | 26 |
|   | 8 | 0 |
| Q | 7 | 23 |
|   | 8 | 0 |

EXAMPLE 14

Test method: 20 g of wheat are treated with an acetone solution of an active ingredient in the amount listed in Table V. 20 adult grain weevils *Calandra granaria* (*Sitophilus granarius*) are placed in each wheat group and incubation is carried out at 29° C. and 60% relative humidity. After 10 days, the parenteral generation is removed and the wheat is further incubated under the same conditions of temperature and humidity until the filial generation hatches. Untreated groups and groups treated with acetone only served as controls. The duration of the test was ca. 50 days. The results, tabulated in Table V, are expressed as percent reduction in the filial generation (number of weevils) in comparison with the controls.

Table V

| Active Ingredient | Dosage ($10^{-x}$ g. a.i./g wheat) | % Reduction |
|---|---|---|
| A | 5 | 100 |
|   | 6 | 100 |
|   | 7 | 32 |
| B | 5 | 100 |
|   | 6 | 65 |
|   | 7 | 0 |
| C | 5 | 93 |
|   | 6 | 18 |
| M | 5 | 50 |
|   | 6 | 23 |
| N | 5 | 40 |
|   | 6 | 12 |
| O | 5 | 0 |
|   | 6 | 0 |

EXAMPLE 15

Test method: 10 g of flour are treated in a large tablet tube with an acetone solution of an active ingredient in the amount listed in Table VI. 10 larvae of *Ephestia Kuhniella* (Mediterranean flour moth) in the last larval stage are placed in each flour group and the larvae are incubated at 25° C. and 60% relative humidity until the adults in the control groups hatch. Untreated flour groups and flour groups treated with acetone served as controls. The duration of the test was 4–5 weeks. The results, tabulated in Table VI, are expressed as percent reduction in the number of normal adults in comparison with the controls (control mortality is 8%).

Table VI

| Active Ingredient | Dosage ($10^{-x}$ g. a.i./g/ flour) | % Reduction |
|---|---|---|
| A | 6 | 100 |
|   | 7 | 100 |
| C | 6 | 100 |
|   | 7 | 100 |
| M | 6 | 76 |
|   | 7 | 51 |
| N | 6 | 56 |
|   | 7 | 0 |
| O | 6 | 38 |
|   | 7 | 24 |

EXAMPLE 16

Test method: 20 g of wheat are treated with an acetone solution of an active ingredient in the amount listed in Table VII. 20 adult beetles of Rhizopertha dominica (lesser grain borer) are placed in each wheat group and the beetles are incubated for 60 days at 25° C. and 60% relative humidity. Untreated wheat groups and wheat groups treated with acetone served as controls. The duration of the test was 60 days. The results, tabulated in Table VII, are expressed as percent reduction in the filial generation (number of beetles) in comparison with the controls.

Table VII

| Active Ingredient | Dosage ($10^{-x}$ g a.i./g wheat) | % Reduction |
|---|---|---|
| A | 5 | 100 |
|   | 6 | 100 |
|   | 7 | 69 |
|   | 8 | 0 |
| F | 5 | 100 |
|   | 6 | 100 |
|   | 7 | 92 |
|   | 8 | 46 |
| M | 5 | 100 |
|   | 6 | 68 |
|   | 7 | 0 |
| N | 5 | 100 |
|   | 6 | 68 |
|   | 7 | 0 |

EXAMPLE 17

Test method: Filter paper discs are treated with an acetone solution of an active ingredient in the amount listed in Table VIII. "Tunnels", formed from the treated discs, are placed in a plastic beaker and 10 larvae of *Blattella germanica* (German cockroach) in the penultimate larval stage are placed in each tunnel. The larvae are fed with dog food and water and incubated at 25° C. and 60% relative humidity until the adults in the control groups hatch. Untreated filter paper discs and filter paper discs treated with acetone served as control. The duration of the test was 3 weeks. The results, tabulated in Table VIII, are expressed as percent reduction in the number of normal adults in comparison with the controls (control mortality is 0%).

Table VIII

| Active Ingredient | Dosage ($10^{-x}$g a.i./cm$^2$) | % Reduction |
|---|---|---|
| A | 6 | 100 |
|   | 7 | 90 |
|   | 8 | 0 |
| M | 6 | 95 |
|   | 7 | 5 |
| N | 6 | 93 |
|   | 7 | 42 |
| O | 6 | 21 |
| P | 6 | 0 |

EXAMPLE 18

Test method: 1 ml of an acetone solution of an active ingredient is mixed with 50 cm$^3$ of earth. 10 larvae of *Leptinotarsa decemlineata* (Colorado potato beetle) in the last larval stage are placed in each earth group and fed with potato tops. The larvae are incubated at 25° C. and 60% relative humidity until the adults in the control earth groups hatch. Untreated earth groups and earth groups treated with acetone served as controls. The duration of the test was 14–20 days. The results, reported in Table IX, are expressed as percent reduction in the number of normal adults in comparison with the controls (control mortality is 12%).

Table IX

| Active Ingredient | Dosage ($10^{-x}$g a.i./cm$^3$ earth) | % Reduction |
|---|---|---|
| A | 5 | 100 |
|   | 6 | 100 |
|   | 7 | 57 |
| M | 5 | 100 |
|   | 6 | 6 |

EXAMPLE 19

A pesticidal composition in the form of an emulsion concentrate containing a compound of formula I and the following ingredients is prepared.

| Ingredient | g/liter |
|---|---|
| Active ingredient, a compound of formula I | 250 |
| N-Methyl-2-pyrrolidone (NMP) | 300 |
| Alkylphenol-ethylene oxide adduct | 35 |
| Calcium salt of dodecylbenzene sulphonic acid | 15 |
| Cycloalkylepoxystearate | 25 |
| Aromatic solvent (mixture of $C_{10}$-alkylbenzenes | to 1000 ml |

The active ingredient is dissolved in N-methyl-2-pyrrolidone. The remaining ingredients are then added and dissolved. The mixture is brought to volume with the aromatic solvent.

To produce a ready-for-use spray liquor, the emulsion concentrate is added to water to spontaneously obtain an emulsion (o/w) which is stable for hours.

EXAMPLE 20

A pesticidal composition, in the form of a powder which is rapidly wetted by water, is prepared from a compound of formula I and the following ingredients.

| Ingredient | % by weight |
|---|---|
| Active ingredient, a compound of formula I | 50 |
| Silicic acid, hydrated (ca 87% S10$_2$) | 5 |
| Sodium lauryl sulfate | 1 |
| Sodium lignosulfonate | 2 |
| Kaolin, mainly Al$_2$[Si$_2$O$_5$] (OH)$_4$ | 42 |

All percentages are by weight based on the total weight of the composition.

The solid active ingredient is homogeneously mixed with the remaining ingredients in a suitable apparatus. The resulting powder is then finely milled in a suitable mill machine (e.g. a pinned disc, hammer, ball, air jet mill etc.) to a particle size necessary for an optimum biological activity and is thereafter again mixed. The resulting spray powder is rapidly wetted by water to yield a suspendable ready-for-use spray liquor.

EXAMPLE 21

A pesticidal composition in the form of a granulate is prepared from a compound of formula I and the following ingredients.

| Ingredient | % by weight |
|---|---|
| Active ingredient, a compound of formula I | 5 |
| Tetrasodium salt of ethylenediaminetetraacetic acid | 1 |
| Pumice stone granulate (0.6–1.0 mm) | 94 |

The pumice stone granulate is placed in a suitable mixing mill and an aqueous solution of the tetrasodium salt of ethylenediaminetetraacetic acid is sprayed therein with continuous stirring. After the mixture is dried at 110° C., the active ingredient, dissolved in a suitable solvent (e.g. methylene chloride), is then sprayed onto the dried mixture. The solvent is evaporated by warming. The resulting granulate can be spread onto the ground or in water either by hand, with suitable granulate sprinklers or from aircraft. The porous structure of the pumice stone results, in many cases, in a desirable delayed release of the active ingredient over a period of time.

We claim:

1. A compound of the formula

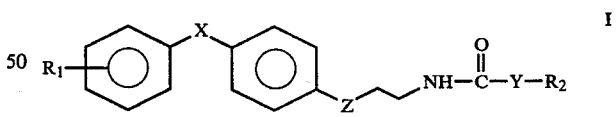

wherein R$_1$ is hydrogen, fluorine, chlorine, alkyl of from one to six carbons, trifluoromethyl, hydroxy or methoxy, X is oxygen, carbonyl, methylene, sulphur or sulfonyl, Z is oxygen, methylene or sulphur, Y is oxygen or sulphur and R$_2$ is alkyl of from one to six carbons.

2. A compound of claim 1 wherein Z is oxygen or sulfur.

3. A compound of claim 1 wherein R$_1$ is hydrogen, Z is oxygen, X is oxygen, methylene or carbonyl, Y is oxygen and R$_2$ is ethyl or isopropyl.

4. A compound of claim 1, 2-(p-benzoylphenoxy)ethylcarbamic acid ethyl ester.

5. A compound of claim 1, 2-(p-phenoxyphenoxy)ethylcarbamic acid ethyl ester.

6. A compound of claim 1, 2-[p-(p-chlorobenzoyl)-phenoxy]ethylcarbamic acid ethyl ester.

7. A compound of claim 1, 2-[p-(p-chlorobenzyl)-phenoxy]ethylcarbamic acid ethyl ester.

8. A compound of claim 1, 2-[p-(o-chlorobenzoyl)-phenoxy]ethylcarbamic acid ethyl ester.

9. A compound of claim 1, 2-[p-[(p-chlorophenylthiol]phenoxy]ethylcarbamic acid ethyl ester.

10. A compound of claim 1, 2-[p-[(p-chlorophenyl)-sulfonyl]-phenoxy]ethylcarbamic acid ethyl ester.

11. A compound of claim 1, 2-[p-(p-toluoyl)-phenoxy]ethylcarbamic acid ethyl ester.

12. A compound of claim 1, 2-[p-(p-tolyloxy)-phenoxy]ethylcarbamic acid ethyl ester.

13. A compound of claim 1, 2-[p-(m-toluoyl)-phenoxy]ethylcarbamic acid ethyl ester.

14. A compound of claim 1, 2-[p-(o-toluoyl)-phenoxy]ethylcarbamic acid ethyl ester.

15. A compound of claim 1, 2-[p-(p-hydroxybenzoyl)-phenoxy]ethylcarbamic acid ethyl ester.

16. A compound of claim 1 2-(p-benzylphenoxy)ethylcarbamic acid ethyl ester.

17. A compound of claim 1, 2-(p-benzoylphenoxy)ethylthiocarbamic acid S-ethyl ester.

18. A compound of claim 1, 2-[p-(phenylsulfonyl)-phenoxy]ethylcarbamic acid ethyl ester.

19. A compound of claim 1, 2-[p-(phenylthio)phenoxy]ethylcarbamic acid ethyl ester.

20. A compound of claim 1, 2-(p-phenoxyphenoxy)ethylthiocarbamic acid S-ethyl ester.

21. A compound of claim 1, 2-[p-(phenylthio)phenoxy]ethylthiocarbamic acid S-ethyl ester.

22. A compound of claim 1, 2-[p-(p-chlorophenoxy)-phenoxy]ethylcarbamic acid ethyl ester.

23. A compound of claim 1, 2-[p-(p-chlorophenoxy)-phenoxy]ethylcarbamic acid isopropyl ester.

24. A compound of claim 1, 2-[p-(m-tolyloxy)phenoxy]ethylcarbamic acid ethyl ester.

25. A compound of claim 1, 2-[p-(p-tert.butylphenoxy)phenoxy]ethylcarbamic acid ethyl ester.

26. A insecticidal composition comprising inert carrier material and, as the active ingredient, a pesticidally effective amount of one or more compounds of the formula

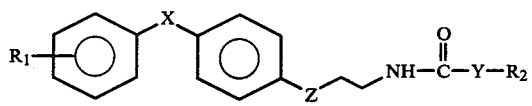

wherein $R_1$ is hydrogen, fluorine, chlorine, alkyl of from one to six carbons, trifluoromethyl, hydroxy or methoxy, X is oxygen, carbonyl methylene, sulphur or sulphonyl, Z is oxygen, methylene, or sulphur, Y is oxygen or sulphur and $R_2$ is alkyl of from one to six carbons.

27. The insecticidal composition of claim 26 where the active ingredient is one or more compounds of formula 1 wherein $R_1$ is hydrogen, Z is oxygen, X is oxygen, methylene or carbonyl, Y is oxygen and $R_2$ is ethyl or isopropyl.

28. The insecticidal composition of claim 26 wherein the active ingredient is 2-(p-benzoylphenoxy)ethylcarbamic acid ethyl ester.

29. The insecticidal pesticidal composition of claim 26 wherein the active ingredient is 2-(p-phenoxyphenoxy)ethylcarbamic acid ethyl ester.

30. A method for controlling insects with comprises application to the area to be protected of a insecticidally effective amount of the composition of claim 26.

31. A method for controlling insects which comprises application to the area to be protected of an insecticidally effective amount of the composition of claim 27.

32. A method for controlling insects which comprises application to the area to be protected of an insecticidally effective amount of the composition of claim 28.

33. A method for controlling insects which comprises application to the area to be protected on an insecticidally effective amount of the composition of claim 29.

* * * * *